US011246548B2

(12) United States Patent
Simmons et al.

(10) Patent No.: US 11,246,548 B2
(45) Date of Patent: Feb. 15, 2022

(54) SYSTEMS FOR VIBRATION DAMPING IN A MOBILE RADIOGRAPHIC IMAGING SYSTEM

(71) Applicant: GE Precision Healthcare LLC, Milwaukee, WI (US)

(72) Inventors: John Matthew Simmons, Queen Creek, AZ (US); Jan Bruening, Salt Lake City, UT (US); David Barker, Salt Lake City, UT (US); Nathan Pack, South Jordan, UT (US)

(73) Assignee: GE Precision Healthcare LLC, Milwaukee, WI (US)

( * ) Notice: Subject to any disclaimer, the term of this patent is extended or adjusted under 35 U.S.C. 154(b) by 169 days.

(21) Appl. No.: 16/690,065

(22) Filed: Nov. 20, 2019

(65) Prior Publication Data

US 2021/0145379 A1  May 20, 2021

(51) Int. Cl.
*A61B 6/00* (2006.01)
*F16F 9/32* (2006.01)

(52) U.S. Cl.
CPC ............ *A61B 6/4405* (2013.01); *A61B 6/447* (2013.01); *A61B 6/4441* (2013.01); *F16F 9/3207* (2013.01)

(58) Field of Classification Search
CPC ............................. A61B 6/4405; A61B 6/4441
See application file for complete search history.

(56) References Cited

U.S. PATENT DOCUMENTS

| 9,144,145 | B2* | 9/2015 | Furst | A61B 6/4452 |
| 9,204,851 | B2 | 12/2015 | Baumann et al. | |
| 2002/0174515 | A1* | 11/2002 | Strong | B60B 33/0015 |
| | | | | 16/110.1 |

* cited by examiner

*Primary Examiner* — Dani Fox
(74) *Attorney, Agent, or Firm* — McCoy Russell LLP

(57) ABSTRACT

Various systems are provided for damping vibration in a mobile radiographic imaging system. In one embodiment, a vibration damping assembly for a C-arm imaging system comprises a pivot element rotatably coupled to a toe portion of the C-arm imaging system and configured to form an interface between the toe portion, a damping element, and a ground surface on which the C-arm imaging system sits.

20 Claims, 5 Drawing Sheets

SYSTEMS FOR VIBRATION DAMPING IN A MOBILE RADIOGRAPHIC IMAGING SYSTEM

FIELD

Embodiments of the subject matter disclosed herein relate to mobile radiographic imaging systems, and more particularly, to systems for vibration damping in mobile radiographic imaging systems.

BACKGROUND

Radiographic imaging systems, such as a C-arm imaging system, may be used in various applications, including medical and industrial applications, to acquire images of the internal features of an object or patient. In a medical environment, a radiographic imaging system may provide a non-invasive means of imaging tissue and bone of a patient, whereas in industrial applications, a radiographic imaging system may provide details of the internal composition and arrangement of an object, machine, etc., without requiring disassembly/opening of the object/machine. Further, mobile radiographic imaging systems, which may comprise one or more moving parts and/or may be transported from location to location via a mobile support system (such as wheels, rails, etc.), may enable the radiographic system to move to new locations easily, increasing the flexibility and usefulness of the radiographic imaging systems. As another example, the mobile radiographic imaging system may be moved to reposition the imaging components of the radiographic imaging system relative to an imaging subject without repositioning the imaging subject.

BRIEF DESCRIPTION

In one embodiment, a vibration damping assembly for a C-arm imaging system comprises a pivot element rotatably coupled to a toe portion of the C-arm imaging system and configured to form an interface between the toe portion, a damping element, and a ground surface on which the C-arm imaging system sits.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below:

FIGS. 3-5 show cross-sectional views of the vibration damping assembly of FIG. 2 in different loaded and unloaded conditions.

FIGS. 2-8 are shown to scale, though other relative dimensions may be used, if desired.

DETAILED DESCRIPTION

Figure 6:
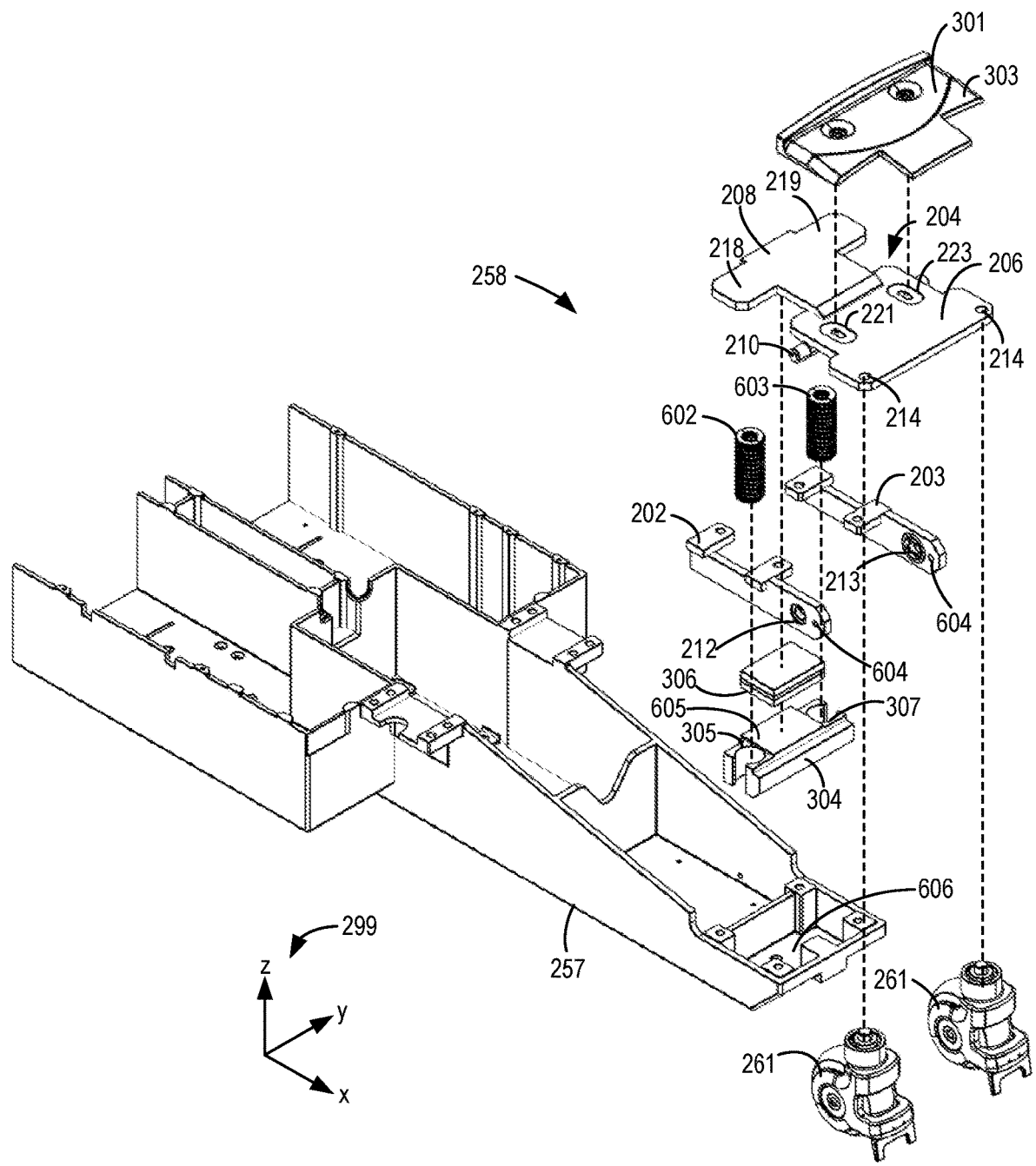
FIG. 6 shows an exploded view of the vibration damping assembly of FIGS. 2-5.
Figure 8:
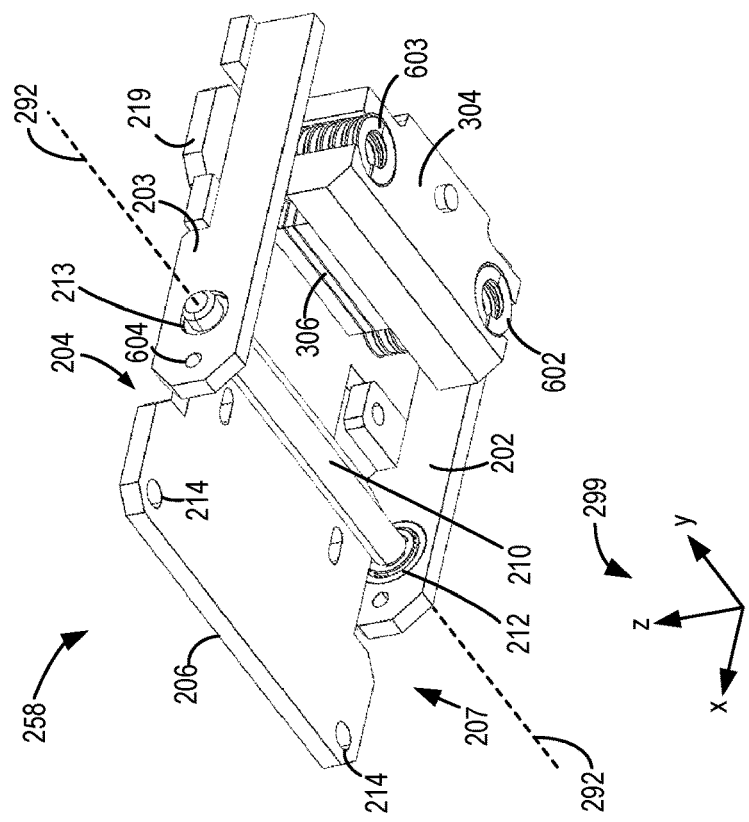
FIG. 8 shows a perspective view of the bottom end of the vibration damping assembly of FIGS. 2-7, with the vibration damping assembly decoupled from the mobile radiographic imaging system.
Figure 7:
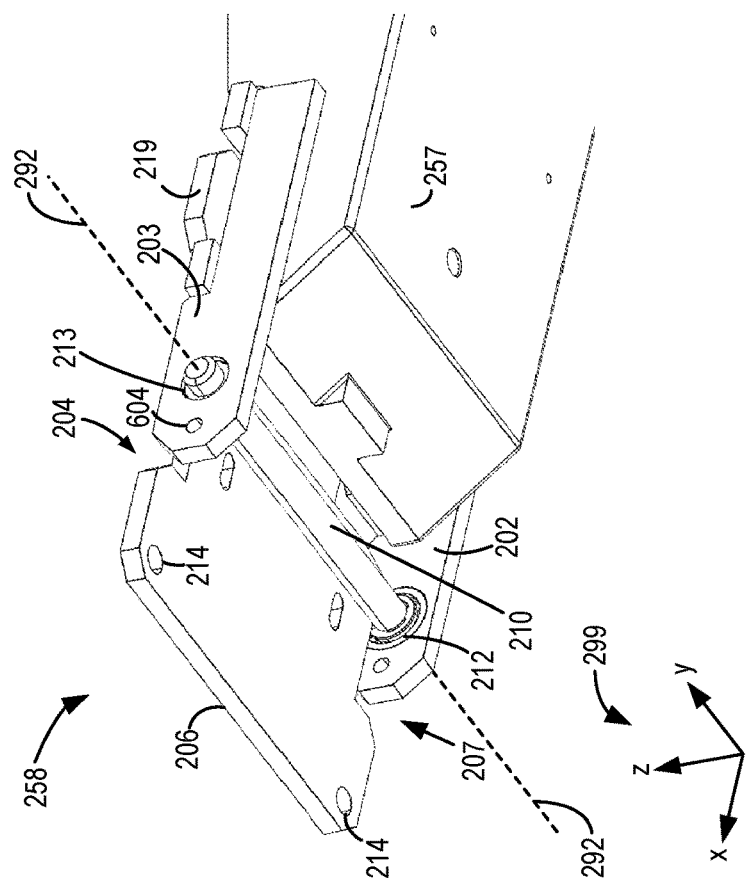
FIG. 7 shows a perspective view of a bottom end of the vibration damping assembly of FIGS. 2-6, with the vibration damping assembly coupled to the mobile radiographic imaging system.

The following description relates to various embodiments for vibration damping of a mobile radiographic imaging system using a vibration damping assembly coupled to an extended toe portion of the mobile radiographic imaging system. A mobile radiographic imaging system, such as the mobile radiographic imaging system shown by FIG. 1, includes a C-arm extending outward from a base unit of the imaging system. The imaging system further includes a toe portion extending outward from the base unit vertically below the C-arm and supporting the imaging system at a ground surface. The toe portion includes a vibration damping assembly, such as the vibration damping assembly shown by FIG. 2, forming an interface between the toe portion and the ground surface. The vibration damping assembly is configured to pivot relative to the toe portion responsive to various load conditions of the toe portion, as shown by FIGS. 3-5, to damp vibration of the toe portion. The vibration damping assembly may include one or more springs and damping elements configured to absorb vibration of the toe portion, as shown by FIG. 6, and the vibration damping assembly may be configured to partially seat within the toe portion, as shown by FIGS. 7-8.

In this way, the vibration damping assembly may reduce vibration of the toe portion, base unit, and/or C-arm during imaging of a subject via the C-arm, and an imaging quality of the imaging system may be increased. For example, the vibration damping assembly may increase a decay rate of vibrations of the imaging system relative to imaging systems that do not include the vibration damping assembly. Because the vibration damping assembly may substantially increase a vibration decay rate through the entire mobile radiographic imaging system, the vibration damping assembly may reduce motion induced blur in images acquired by the imaging system. The vibration damping assembly may damp vibration of the imaging system passively, without being driven by a motor and without input by other actuators or a user of the imaging system. By positioning the vibration damping assembly at the end of the extended toe portion extending in a same direction as the C-arm, the vibration damping assembly may reduce vibration (e.g., an amplitude of vibration) produced from rotation of the C-arm during imaging of a subject and vibration produced from a motor used to drive the rotation of the C-arm.

In one embodiment, the vibration damping assembly comprises a pair of support arms including a pair of pivot pin receiving holes, where the pair of support arms are rigidly affixed to the toe portion of the mobile medical imaging system. A pivot plate pivotally couples to the pair of support arms via insertion of a pivot pin through the pair of pivot pin receiving holes. The pivot plate includes a forward portion and a rearward portion, with one or more wheels coupled to an underside of the forward portion. The pivot pin extends between the forward portion and the rearward portion of the pivot plate. A damping element includes a first side affixed to the rearward portion of the pivot plate and a second side affixed to the toe portion of the medical imaging system.

As used herein, mobile radiographic imaging systems will be understood to include imaging systems wherein the imaging components of the imaging system are moveable and/or imaging systems wherein the imaging system itself may be moved from location to location via a mobile support system (e.g., a plurality of wheels, rails, etc.). Although the vibration damping assembly is described herein as configured to damp vibration of a C-arm imaging system, it will be appreciated that in some examples, the vibration damping assembly may be employed with a different radiographic imaging system, such as an industrial imaging system (non-medical), an immobile imaging system wherein one or more components of the imaging system is repositionable, or an imaging system of a different imaging modality (e.g., visual, positron emission tomography, magnetic resonance imaging, computed tomography, etc.).

As used herein, down refers to a direction of gravitational acceleration and may be described relative to a ground surface. Therefore, terms such as downward, as used herein, will be understood to refer to movement or extension in a direction of the gravitational acceleration (or toward a ground surface). Similarly, the term underside, as used herein, refers to a side of a component facing a ground surface/facing in the direction of gravitational acceleration. Similarly, the term up, as used herein, refers to a direction opposite the direction of gravitational acceleration and may be described relative to a ground surface. Therefore, terms such as upward will be understood to refer to movement or extension in a direction opposite the direction of gravitational acceleration. Similarly, the terms top, upper portion, upper side, and other similar terms will be understood to refer to a portion or side of a component facing up or at an uppermost section of a component.

Figure 1:
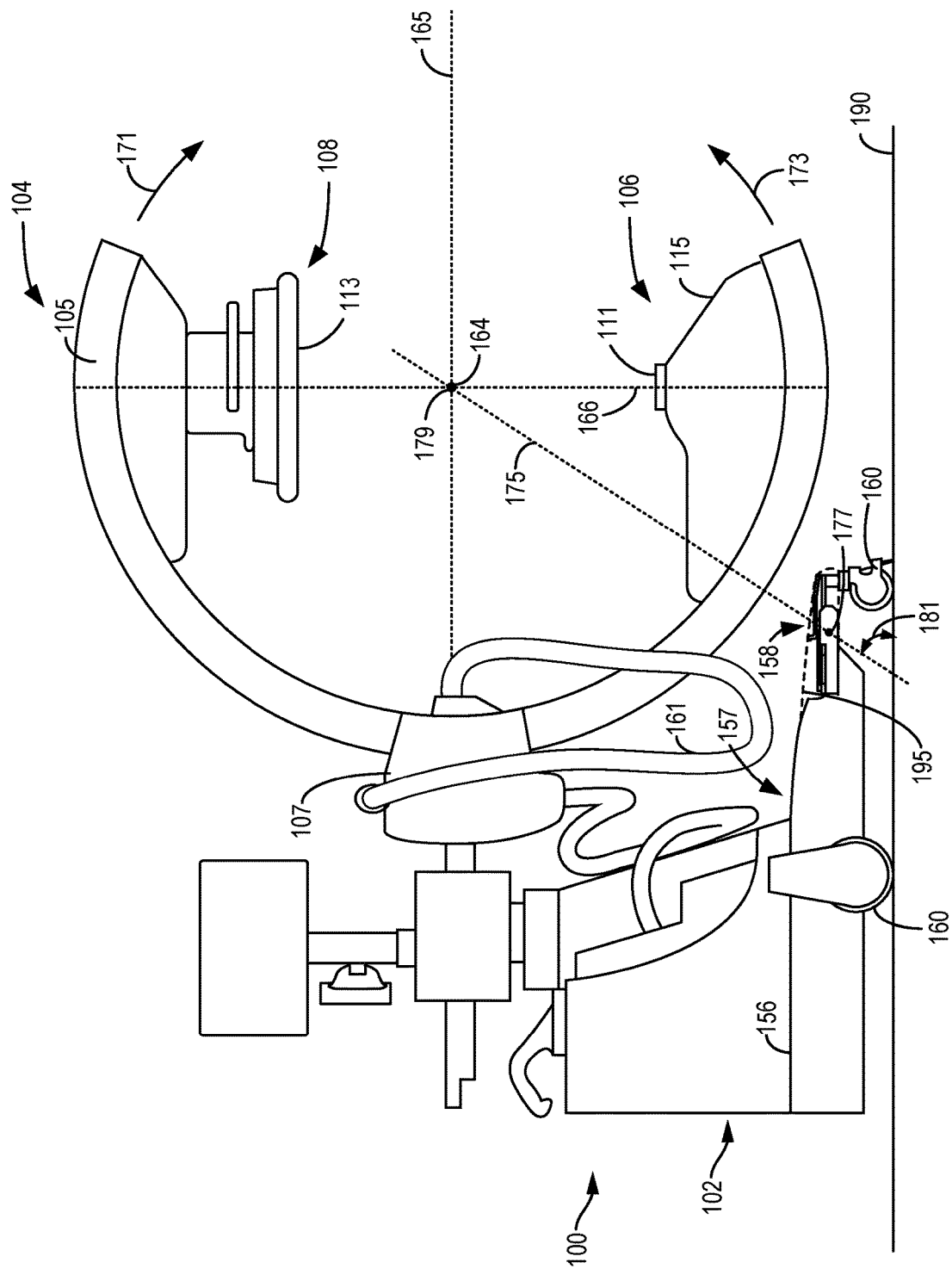
FIG. 1 shows a mobile radiographic imaging system including a vibration damping assembly.

Referring to FIG. 1, a side view of a mobile medical imaging system 100 is shown, where the mobile medical imaging system includes a C-arm 104 with an x-ray source 106 positioned opposite to an x-ray detector 108. The imaging system 100 additionally includes a base unit 102. A base portion 156 of the base unit 102 includes a plurality of wheels 160 for supporting the mobile medical imaging system 100 and/or transporting the mobile medical imaging system 100 from one location to another. Each wheel 160 may include a brake configured to lock the wheel into a fixed position and reduce a likelihood of the movement of the mobile medical imaging system 100. Further, the base portion 156 includes a toe portion 157 extending in an outward direction relative to the base portion 156 and toward the C-arm 104 (e.g., parallel to a ground surface 190 on which the imaging system 100 sits). The toe portion 157 includes a vibration damping assembly 158, to which one or more of the wheels 160 is coupled. The vibration damping assembly 158 may comprise one or more damping elements. The vibration damping assembly 158 is configured to reduce vibrations in mobile medical imaging system 100 and to decrease a vibration decay time for vibrations which may arise from repositioning of C-arm 104 (e.g., rotation of the C-arm 104) and/or movement of imaging system 100 (e.g., from one location to another).

The C-arm 104 includes a C-shaped portion 105 connected to an extended portion 107. As an example, the C-shaped portion 105 may be configured to rotate at least 180 degrees in opposing directions (e.g., around a rotational axis 165). The C-shaped portion 105 is additionally rotatable about a rotational axis 164 via the extended portion 107. For example, the C-shaped portion 105 may be rotatably coupled to the extended portion 107 such that the C-shaped portion 105 may rotate relative to the extended portion 107 in a first direction 171 and/or an opposing, second direction 173 around the rotational axis 164. The C-shaped portion 105 may be rotated as described above in order to adjust the x-ray source 106 and detector 108 (positioned on opposite ends of the C-shaped portion of the C-arm 104 along an axis 166, where axis 166 intersects rotational axis 164 and extends radially relative to rotational axis 164) through a plurality of positions.

During an imaging operation, a portion of a patient's body placed in a clearance (e.g., gap) formed between the x-ray source 106 and detector 108 may be irradiated with radiation from the x-ray source. For example, x-ray source 106 may comprise an x-ray tube housed within a housing 115, and x-ray radiation generated by the x-ray source 106 may emit from an outlet 111 of the housing 115 and may be intercepted by a detection surface 113 of the detector 108. The radiation may penetrate the portion of the patient's body being irradiated and travel to the detector 108 where the radiation is detected. By penetrating the portion of the patient's body placed between the x-ray source 106 and detector 108, an image of the patient's body is captured and relayed to an electronic controller of the mobile medical imaging system 100 (e.g., via an electrical connection line, such as an electrically conductive cable 161). In one example, the display monitor may display images taken and processed by the mobile medical imaging system 100 as they are taken and during the imaging procedure (e.g., in real-time). Instructions may be entered into the imaging system 100 via one or more input devices. Instructions may include x-ray source activation instructions, source voltage/current instructions, source rotation instructions, image display instructions, image storing instructions, etc.

The base unit 102 may include the electronic controller (e.g., a control and computing unit) that processes instructions or commands sent from the user input devices during operation of the mobile medical imaging system 100. The base unit 102 may also include an internal power source (not shown) that provides electrical power to operate the imaging system 100. Alternatively, the base unit 102 may be connected to an external electrical power source to power the imaging system 100. A plurality of connection lines (e.g., electrical cables, such as electrically conductive cable 161) may be provided to transmit electrical power, instructions, and/or data between the x-ray source 106, detector 108, and the control and computing unit. The plurality of connection lines may transmit electrical power from the electrical power source (e.g., the internal and/or external source) to the x-ray source 106 and detector 108.

The C-arm 104 may be adjusted to a plurality of different positions by rotation of the C-shaped portion 105 of the C-arm 104 (e.g., via the coupling between the extended portion 107 and C-shaped portion 105). For example, in an initial, first position shown by FIG. 1, the detector 108 may be positioned vertically above the x-ray source 106 relative to the ground surface 190 on which the imaging system 100 sits, with axis 166 arranged normal to the ground surface 190 intersecting a midpoint of each of the outlet 111 of x-ray source 106 and detection surface 113 of detector 108. The C-arm 104 may be adjusted from the first position to a different, second position by rotating the C-shaped portion 105. In one example, the second position may be a position in which the x-ray source 106 and detector 108 are rotated 180 degrees together relative to the first position, such that the x-ray source 106 is positioned vertically above the detector 108, with axis 166 intersecting the midpoint of the outlet 111 of the x-ray source 106 and the midpoint of the detection surface 113 of the detector 108. When adjusted to the second position, the x-ray source 106 may be positioned vertically above the rotational axis 164 of the C-shaped portion 105 of the C-arm 104, and the detector 108 may be positioned vertically below the rotational axis 164.

Movement of C-arm 104, as discussed above, is accomplished by acceleration and deceleration of the C-shaped portion 105 of the C-arm 104 (e.g., via a motor of the imaging system 100 configured to drive rotation of the C-shaped portion 105 of the C-arm 104), which may induce vibrations in C-arm 104 and/or the imaging components (x-ray detector 108 and x-ray source 106) attached thereto. Further, vibrations associated with operation of the components coupled to the C-arm 104, such as a vibration of an x-ray tube of the x-ray source 106, may contribute to an overall vibration of the C-arm 104. Such vibrations are undesirable, as the vibrations may degrade image clarity by introducing motion blur in images acquired by the imaging system 100. For imaging systems that do not include the vibration damping assembly, a decay rate of the vibrations may be quite large such that an amplitude of the vibrations decreases slowly. For example, moving an imaging system that does not include the vibration damping assembly from one location to another may result in oscillation of a C-arm or other components of the imaging system, which may delay imaging of a subject as an operator of the imaging system (e.g., a clinician) waits for the amplitude of the oscillations to slowly decrease. The time spent waiting for the oscillations to decrease may increase an overall imaging time of the subject and result in an increased cost of the imaging. Further, because the amplitude of the oscillations may be quite high, a likelihood of degradation of the C-arm and/or other components may be increased (e.g., degradation resulting from undesired movement of the C-arm and/or other components).

Because the C-arm 104 is positioned away from the base unit 102 via extended portion 107, the C-arm may act as a mass at an end of a cantilever. As such, acceleration and/or deceleration of the C-arm 104 may induce a characteristic vibration of the C-arm 104 (e.g., in an up and down direction, toward and away from ground surface 190). By providing the vibration damping assembly 158 at the end of toe portion 157, the toe portion 157 may transmit (e.g., transfer) the vibration of the C-arm 104 to the vibration damping assembly 158 (e.g., via a cover 195 of the toe portion 157), where the vibration may be absorbed (e.g., damped) by the vibration damping assembly 158. As a result, the vibration damping assembly 158 may increase the decay rate of the amplitude of vibration in the imaging system 100, which may result in increased image quality and/or increased productivity (e.g., decreased oscillation time of the C-arm 104 and other components, resulting in a decreased imaging time).

Although the vibration damping assembly 158 is shown coupled to the toe portion 157 of imaging system 100 in FIG. 1, in some examples, the vibration damping assembly 158 may be coupled to a toe portion of an imaging system having different relative dimensions compared to the imaging system 100 shown by FIG. 1. For example, a toe portion of an imaging system may have a shortened length relative to the toe portion 157 of imaging system 100 shown by FIG. 1, and as a result, the imaging system may have different vibration characteristics (e.g., oscillation frequencies). In some examples, an imaging system may include components different than those shown by FIG. 1 that result in different vibration characteristics, such as x-ray tubes configured to operate at higher speeds relative to an x-ray tube of the x-ray source 106 of imaging system 100.

Due to the possibility of different vibration characteristics for different imaging systems, the vibration damping assembly 158 may include one or more components selected based on a configuration of the imaging system to which the vibration damping assembly 158 is coupled. For example, the vibration damping assembly 158 may include one or more springs and/or damping elements that may be replaceable in order to adjust (e.g., tune) a vibration absorption characteristic of the vibration damping assembly 158. As one example, the vibration damping assembly 158 may include a pair of springs (similar to the examples described further below), and the springs may be replaceable such that a stiffness of each spring may be selected according to the vibrational characteristics of the imaging system to which the vibration damping assembly 158 is coupled. As another example, the vibration damping assembly 158 may include a deformable member (e.g., deformable damping pad, similar to the examples described below), and a stiffness of the deformable member may be selected according to the vibrational characteristics of the imaging system to which the vibration damping assembly 158 is coupled. In this way, a vibration damping characteristic of the vibration damping assembly 158 may be increased for various different imaging systems.

In some examples, a length of the vibration damping assembly 158 may be selected according to a configuration of an imaging system to which the vibration damping assembly 158 is coupled in order to achieve a pre-determined position of the vibration damping assembly 158 relative to a center of rotation of a C-shaped portion of a C-arm of the imaging system. For example, as shown by FIG. 1, an axis 175 intersects a center of rotation 179 of the C-shaped portion 105 of the C-arm 104 as well as a rotational axis 177 of the vibration damping assembly 158. In some examples, the center of rotation 179 may be a center of mass of the C-arm 104. The vibration damping assembly 158 may be coupled to the toe portion 157 in a configuration in which an angle 181 between the axis 175 and the ground surface 190 is a pre-determined angle selected to reduce an amount of vibration of the imaging system 100 based on vibrational characteristics of the imaging system (e.g., a frequency, such as a peak frequency, of vibration resulting from movement of the imaging system and/or C-arm, vibration from operation of the x-ray source 106, etc.). As one example, the angle 181 may be 60 degrees. In other examples, however, the angle 181 may be a different number of degrees (e.g., 45 degrees, 50 degrees, 70 degrees, etc.) based on the vibrational characteristics.

Figure 2:
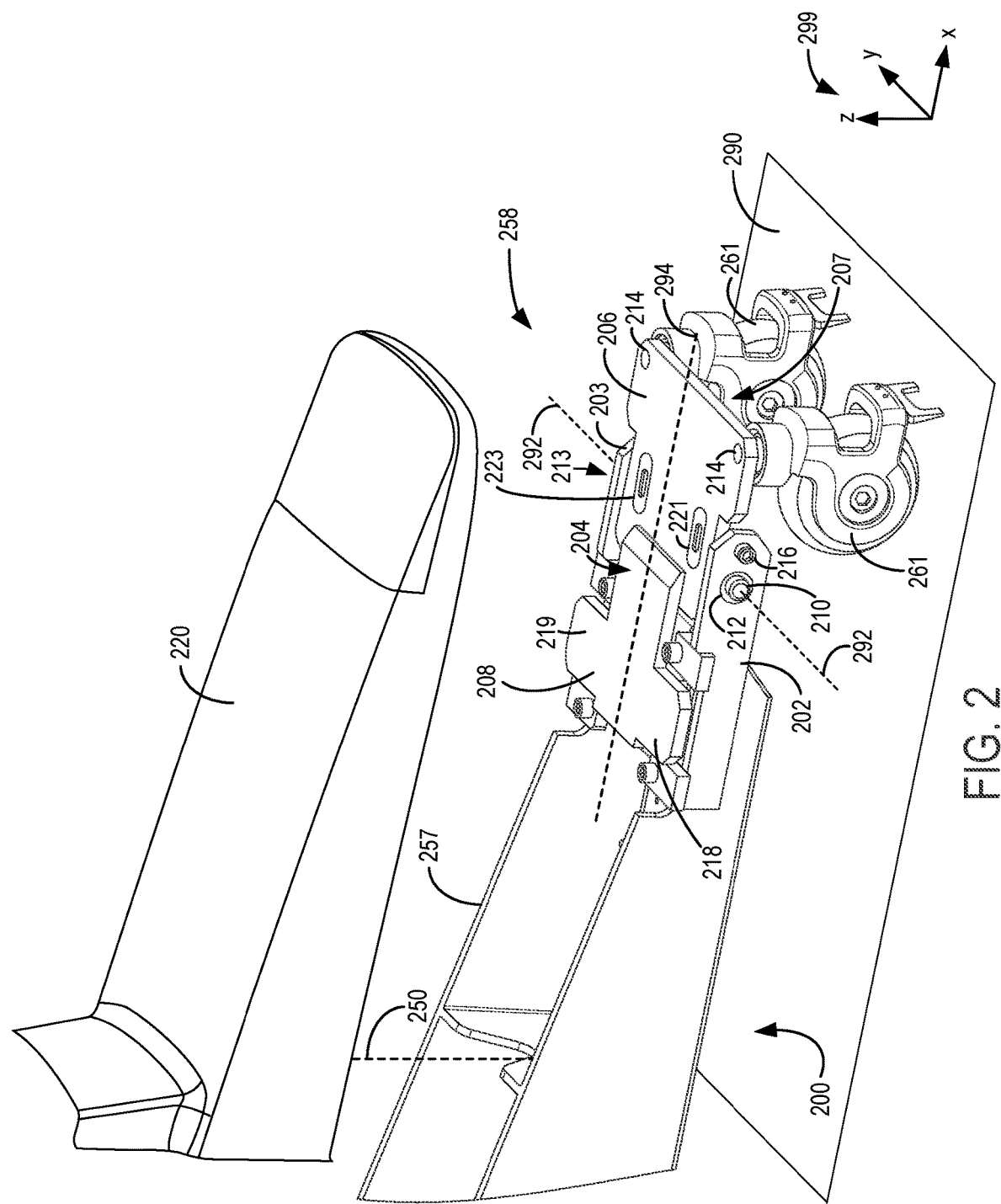
FIG. 2 shows a perspective view of a vibration damping assembly of a mobile radiographic imaging system.
Figures 3, 4, 5:
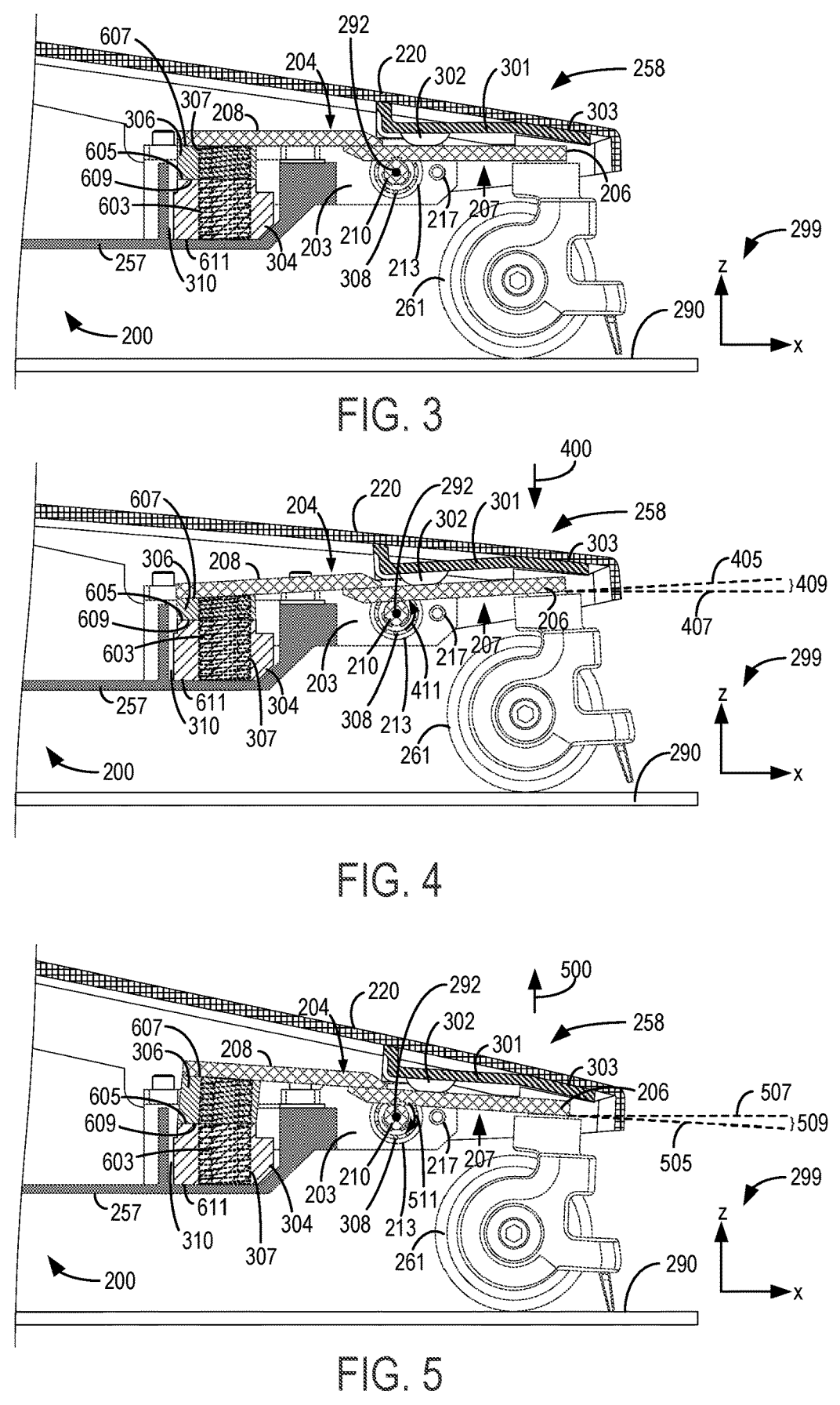

Referring now to FIG. 2, a perspective view of a vibration damping assembly 258 of an imaging system 200 is shown. In some examples, the vibration damping assembly 258 and imaging system 200 may be the same as the vibration damping assembly 258 and imaging system 100 described above with reference to FIG. 1. In the view shown by FIG. 2, a cover 220 (e.g., similar to cover 195 shown by FIG. 1) of a toe portion 257 is shown separated from the vibration damping assembly 258 and toe portion 257. The cover 220 may couple to the toe portion 257 along an assembly axis 250, with the axis 250 arranged normal to a ground surface 290 on which the imaging system 200 sits (e.g., similar to ground surface 190 shown by FIG. 1). Reference axes 299 are included in FIGS. 2-9 for comparison of the views shown.

Vibration damping assembly 258 may include a pair of support arms (which may be referred to herein as mounting brackets), including a first support arm 202 and a second support arm 203 configured to mount to toe portion 257 of the imaging system 200 (where toe portion 257 may be similar to toe portion 157 described above). Each support arm may include a respective opening configured to receive a pivot pin. For example, first support arm 202 may include an opening 212, and second support arm may include an opening 213 (shown by FIGS. 3-6 and indicated generally in FIG. 2), with a midpoint of each of the opening 212 and opening 213 intersected by rotational axis 292 such that the opening 212 and opening 213 are each arranged along the rotational axis 292. Each of the support arms may be fixedly coupled to the toe portion 257 such that each support arm does not move (e.g., rotate) relative to the toe portion 257.

Each of the support arms may be coupled to the toe portion via one or more fasteners (e.g., bolts). The support arms may extend away from toe portion 157 in a direction substantially parallel to ground surface 290 and toward the C-arm of the imaging system 200. The support arms are offset from each other along rotational axis 292 at opposing sides of a pivot plate 204 (which may be referred to herein as a pivot element), and each support arm extends in a direction between a forward portion 206 (e.g., forward end) and a rearward portion 208 (e.g., rearward end) of pivot plate 204. A length between the support arms may be approximately a same amount of length as a length of the pivot plate 204 in the direction of the rotational axis 292. Each support arm may include a corresponding stop, such as a stopper pin 216 of first support arm 202 and a stopper pin 217 of the second support arm 203 (shown by FIGS. 3-5). The stopper pin 216 and stopper pin 217 may each limit a rotation of the pivot plate 204 in a first direction during conditions in which the pivot plate 204 is rotated such that forward portion 206 moves toward the ground surface 290 (e.g., in a loaded condition of the pivot plate 204, in which vibrational load is applied to the vibration damping assembly 258 through the toe portion 257). For example, as the pivot plate 204 rotates with the forward portion 206 rotating toward the ground surface 290, the forward portion 206 may be prevented from rotating beyond a pre-determined angle (e.g., 3.5 degrees) due to interference between the stopper pins 216 and 217 and the forward portion 206 of the pivot plate 204 at an underside 207. The stopper pin 216 may be positioned at a side of the first support arm 202 arranged at the forward portion 206 of pivot plate 204, and stopper pin 217 may be similarly positioned at a side of the second support arm 203 arranged at forward portion 206 (e.g., adjacent forward portion 206).

Pivot plate 204 may be pivotally coupled to the pair of support arms by a pivot pin 210, with the pivot pin 210 disposed within each of the opening 212 and the opening 213. Forward portion 206 of pivot plate 204 may be configured to couple to one or more wheels 261 at the underside 207 of the pivot plate 204, and the wheels 261 may support a weight of the imaging system 200. For example, forward portion 206 may include one or more openings 214 each configured to couple to one of the respective wheels 261 (e.g., via fasteners such as bolts, etc.). Rearward portion 208 of the pivot plate 204 may include a pair of flanges, including a first flange 218 and a second flange 219, with each flange configured to engage with a corresponding biasing member of the vibration damping assembly 258 as described below. A travel (e.g., rotation) of the pivot plate 204 may be limited by engagement of the first flange 218 and second flange 219 with the first support arm 202 and second support arm 203, respectively, at a side of each support arm opposite to the forward portion 206 of pivot plate 204 (e.g., opposite to the stopper pins 216 and 217). For example, during conditions in which pivot plate 204 is rotated in a direction such that the rearward portion 208 moves toward the toe portion 257, the first flange 218 and second flange 219 may interfere with the first support arm 202 and second support arm 203, respectively, in order to stop the movement of the rearward portion 208 toward the toe portion 257.

The pivot pin 210 is arranged at the forward portion 206 of the pivot plate 204 and extends in a direction between the opening 212 of the first support arm 202 and opening 213 of the second support arm 203, perpendicular to a direction of extension of the toe portion 257 from a base portion of the imaging system (e.g., base portion 156) and coaxial with rotational axis 292. In this configuration, pivot plate 204 is rotatably coupled to the toe portion 157 via the pivot pin 210 seated within the opening 212 of the first support arm 202 and opening 213 of the second support arm 203, with the support arms fixedly coupled to the toe portion 157. Pivot plate 204 may rotate relative to the toe portion 157 around the rotational axis 292.

As described further below, a rearward portion 208 of pivot plate 204 may be coupled to one or more damping elements (e.g., deformable damping members, such as damping pads and/or springs), and the one or more damping elements may be partially disposed within an interior of the toe portion 257. The damping elements may expand or compress responsive to a load applied to the pivot plate 204 (e.g., due to the load causing a rotation of the pivot plate 204 toward, or away from, the damping elements). For example, during conditions in which the pivot plate 204 rotates in a direction away from the damping elements, the damping elements may expand, and during conditions in which the pivot plate 204 rotates toward the damping elements, the damping elements may compress. In this way, vibrations of the imaging system 200 may be transferred to the damping elements via the pivot plate 204 and damped by the damping elements.

During operation of the imaging system 200, vibrations of the imaging system 200 may be transferred to the pivot plate 204 from the toe portion 257. For example, as shown by FIGS. 3-6 and described further below, the toe portion 257 may impart different vibrational loads on the vibration damping assembly 258, and the pivot plate 204 may rotate relative to the toe portion 257 in order to damp the vibrational loads. The pivot plate 204 may include a cover plate forming an interface between cover 220 and the pivot plate 204. In some examples, vibration of the imaging system may additionally transfer from the imaging system to the pivot plate 204 via the cover plate (e.g., via one or more protrusions of the cover plate shaped to engage with counterpart grooves or slots of the pivot plate 204, such as a slot 221 and a slot 223). The rotation of the pivot plate 204 may compress and/or expand one or more biasing members of the vibration damping assembly 258, such as springs and/or other damping elements, in order to damp the vibration of the imaging system 100.

Referring now to FIGS. 3-5, cross-sectional views of the vibration damping assembly 258 are shown for different loaded and unloaded conditions of the vibration damping assembly 258. For example, FIG. 3 shows vibration damping assembly 258 without vibrational loading (e.g., without load applied to the vibration damping assembly 258 due to a vibration or motion of the imaging system 200), FIG. 4 shows vibration damping assembly 258 in a first loaded position (e.g., with load applied to the vibration damping assembly 258 in a first direction due to vibration and/or motion of the imaging system 200), and FIG. 5 shows vibration damping assembly 258 in a second loaded position (e.g., with load applied to the vibration damping assembly 258 in a second direction due to vibration and/or motion of the imaging system 200). FIGS. 3-5 show rearward portion 208 of pivot plate 204 coupled to a damping element 306, which compresses or expands as the load on pivot plate 204 changes in order to damp vibrational motion of the imaging system 200. The cross-sectional views shown by FIGS. 3-5 are taken along axis 294, shown by FIG. 2.

Referring to FIG. 3, the vibration damping assembly 258 is shown without vibrational loading. As one example, in the condition shown by FIG. 3, the imaging system 200 is not undergoing vibration (e.g., vibration due to movement of the imaging system, such as rotation of the C-arm of the imaging system, or operation of components of the imaging system, such as the x-ray source). As a result, pivot plate 204 of the vibrational damping assembly 258 is in a neutral position (e.g., non-rotated position). In this position, the pivot plate 204 is arranged parallel with the ground surface 290 and is not rotated around the rotational axis 292. Although pivot plate 204 is shown parallel with ground surface 290 in the neutral position, in other configurations, the neutral position of pivot plate 204 (e.g., the position of the pivot plate 204 without vibrational loading) may be a different position (e.g., pivot plate 204 may not be arranged parallel to ground surface 290).

The vibrational damping assembly 258 includes damping element 306 positioned at the underside 207 of the pivot plate 204 (e.g., coupled to the underside 207 of pivot plate 204 at rearward portion 208) and between the rearward portion 208 and an upper surface 605 of a biasing member housing 304. A first side 607 of damping element 306 may be coupled (e.g., adhered) to the underside 207 of the pivot plate 204 at the rearward portion 208, and an opposing, second side 609 of the damping element 306 may be coupled (e.g., adhered) to upper surface 605 of the biasing member housing 304. In this configuration, the damping element 306 forms an interface between the biasing member housing 304 and the rearward portion 208 of pivot plate 204.

The biasing member housing 304 may be seated within a recess 310 of the toe portion 157 and may house one or more biasing members (e.g., springs). For example, in the view shown by FIG. 3, a spring 603 is shown seated within an opening 307 (e.g., a channel or passage) of the biasing member housing 304, with the spring 603 and opening 307 shown in broken lines to indicate that the spring 603 and opening 307 are not intersected by the plane of the cross-sectional view (e.g., not positioned along axis 294, and seated adjacent to damping element 306). By seating the spring 603 within the opening 307 of the biasing member housing 304, the biasing member housing 304 may maintain a position of the spring 603 relative to the toe portion 157 and pivot plate 204 as the spring 603 engages with toe portion 157 at the recess 310 and pivot plate 204. Biasing member housing 304 may further include an opening 305 (e.g., a channel or passage) housing a second spring 602, as shown by FIG. 6. Each of the openings 307 and 305 may extend from upper surface 605 of biasing member housing 304 to a lower surface 611 of biasing member housing 304, with the lower surface 611 configured to be in face-sharing contact with a counterpart surface of the recess 310 of the toe portion 257. During conditions in which vibrational load is applied to the vibration damping assembly 258 (e.g., as described below with reference to FIGS. 4-5), the springs 602 and 603 may compress and/or expand to damp the vibration of the imaging system (e.g., decrease an amplitude of the vibrational load). The springs 602 and 603 may be fixedly coupled to each of the pivot plate 204 at the rearward portion 208 and the toe portion 257 (e.g., at the surface of the toe portion 257 positioned in face-sharing contact with the lower surface 611 of the biasing member housing 304) in order to bias the pivot plate 204 toward the neutral position (e.g., toward the unloaded condition and position in which the pivot plate 204 is arranged parallel with the ground surface 290).

The damping element 306 may be maintained in a partially compressed condition while the vibration damping assembly 258 is in the neutral position. In this configuration, the damping element 306 may expand and/or compress responsive to rotation of the pivot plate 204 around the rotational axis 294 via the pivot pin 210. In some embodiments, damping element 306 comprises one or more damping pads (e.g., polyurethane pads), wherein a stiffness and/or damping coefficient of the damping pads may be selected based on an expected range of vibrational loading of the imaging system 200. For example, the damping coefficient of the damping pads may be selected such that the damping element 306 provides increased reduction of vibrations within a pre-determined frequency range and for a wide range of temperatures. In other examples, the damping element 306 may include a different type of damping configuration (e.g., damping element 306 may be a dashpot).

Each of the pivot pin 210 and stopper pin 216 may have substantially circular cross-sections. Pivot pin 210 may be substantially cylindrical in shape, with a longitudinal extent in a direction perpendicular to a direction of extension of toe portion 157, and parallel to ground surface 190. The cylindrical shape of pivot pin 210 facilitates smooth rotation of pivot plate 204 relative to support arms 202, via rotation of pivot pin 210 within pivot pin receiving openings 212. Pivot pin receiving openings 212 may include grease or other lubricant to control an amount of friction between pivot pin 210 and pivot pin receiving openings 212. In some embodiments, pivot pin receiving openings 212 may comprise ball bearings 308, located between an outer diameter of pivot pin 210 and an inner diameter of pivot pin receiving openings 212, facilitating smooth rotation of pivot pin 210 within pivot pin receiving openings 212. In some embodiments, an amount of friction between pivot pin 210 and pivot pin receiving openings 212 may be selected to achieve a desired rate of vibration decay, as the friction between pivot pin 210 and pivot pin receiving openings 212 may provide additional damping of vibration of the mobile medical imaging system 100.

Cover 220 is shown positioned over vibration damping assembly 258, with a cover plate 301 forming an interface between the cover 220 and pivot plate 204. An upper surface 303 of cover plate 301 may be positioned in face-sharing contact with cover 220, and protrusions 302 may be positioned in face-sharing contact with the forward portion 206 of pivot plate 204. The cover plate 301 may include two protrusions 302, with each protrusions configured to engage with a corresponding slot of the pivot plate 204 (e.g., slot 221 and slot 223). Cover plate 301 may act to couple the cover 220 to the pivot plate 204 while enabling a movement of the cover 220 and pivot plate 204 relative to each other.

Referring now to FIG. 4, vibration damping assembly 258 is shown under a first load condition. In the condition shown by FIG. 4, load is applied to the pivot plate 204 in a first direction 400 (e.g., a direction toward from the ground surface 290). For example, as the imaging system 200 vibrates, the toe portion 257 may move in the first direction 400, toward from the ground surface 290. As a result of the interface between the vibration damping assembly 258 and the toe portion 257, as well as the biasing of the pivot plate 204 by the springs 603 and 602 and the damping element 306, the pivot plate 204 pivots around the rotational axis 292 such that the rearward portion 208 moves in the first direction 400. The pivot plate 204 may rotate (e.g., pivot) about pivot pin 210 seated within the pivot pin receiving openings (e.g., openings 212 and 213) of support arms 202, resulting in pivot plate 204 being rotated at an angle relative to ground surface 290. As one example, an angle 409 between an axis 405 parallel with the pivot plate 204 in the first loaded condition and an axis 407 parallel to the ground surface 290 may be 3.5 degrees. However, during some conditions (e.g., conditions in which load is applied to the pivot plate 204 in the same first direction 400, but with a smaller magnitude), the angle 409 may be a different angle (e.g., 1 degree, 2 degrees, etc.).

In the first load condition shown by FIG. 4, rearward portion 208 of pivot plate 204 rotates downward (e.g., toward ground surface 290) and increases an amount of compression of the damping element 306 and springs 602 and 603. Correspondingly, as pivot pin 210 rotates within pivot pin receiving openings 212, gliding along ball bearings 308, the forward portion 206 of pivot plate 204 rotates upwards (e.g., away from the ground surface 290). While in the first load condition, the pivot plate 204 is biased toward the neutral position shown by FIG. 3, such that when the load is removed, the pivot plate 204 rotates back toward the neutral position around the rotational axis 292. As an example operation, an initial position of the pivot plate 204 may be the neutral position shown by FIG. 3. As a load is applied to the pivot plate 204 in the first direction 400 due to a vibration of the imaging system 200, the pivot plate 204 may rotate around the rotational axis 292 in first rotational direction 411, compressing the damping element 306 and springs 602 and 603 and damping the vibration. Because the pivot plate 204 is biased toward the neutral position, the pivot plate 204 may then rotate in an opposing direction (e.g., second rotational direction 511, shown by FIG. 5) to return toward the neutral position.

Referring to FIG. 5, vibration damping assembly 258 is shown under a second load condition. In the condition shown by FIG. 5, load is applied to the pivot plate 204 in a second direction 500 (e.g., a direction away from the ground surface 290), opposite to the first direction 400 shown by FIG. 4. For example, as the imaging system 200 vibrates, the toe portion 257 may move in the second direction 500, away from the ground surface 290. As a result of the interface between the toe portion 257 and the vibration damping assembly 258, as well as the biasing of the pivot plate 204 by the springs 603 and 602 and the damping element 306, the pivot plate 204 pivots around the rotational axis 292 such that the rearward portion 208 moves in the second direction 500.

The pivot plate 204 may rotate (e.g., pivot) about pivot pin 210 seated within the pivot pin receiving openings (e.g., openings 212 and 213) of support arms 202, resulting in pivot plate 204 being rotated at an angle relative to ground surface 290 responsive to the load applied to the pivot plate 204. As one example, an angle 509 between an axis 505 parallel with the pivot plate 204 in the first loaded condition and an axis 507 parallel to the ground surface 290 (and parallel with axis 407 shown by FIG. 4) may be 3.5 degrees. However, during some conditions (e.g., conditions in which load is applied to the pivot plate 204 in the same second direction 500, but with a smaller magnitude), the angle 409 may be a different angle (e.g., 1 degree, 2 degrees, etc.).

In the second load condition shown by FIG. 5, rearward portion 208 of pivot plate 204 rotates upward (e.g., away from ground surface 290) and decreases an amount of compression of the damping element 306 and springs 602 and 603. Correspondingly, as pivot pin 210 rotates within pivot pin receiving openings 212, gliding along ball bearings 308, the forward portion 206 of pivot plate 204 rotates downward (e.g., toward the ground surface 290). While in the second load condition, the pivot plate 204 is biased toward the neutral position shown by FIG. 3, such that when the load is removed, the pivot plate 204 rotates back toward the neutral position around the rotational axis 292. As an example operation, an initial position of the pivot plate 204 may be the neutral position shown by FIG. 3. As a load is applied to the pivot plate 204 in the second direction 500 due to a vibration of the imaging system 200, the pivot plate 204 may rotate around the rotational axis 292 in second rotational direction 511, expanding the damping element 306 and springs 602 and 603 and damping the vibration. Because the pivot plate 204 is biased toward the neutral position, the pivot plate 204 may then rotate in an opposing direction (e.g., first rotational direction 411, shown by FIG. 4) to return toward the neutral position.

Thus, FIGS. 3-5 illustrate the rotation of pivot plate 204 under varying loads, which may arise from vibrations of the imaging system (e.g., vibrations produced by the C-arm coupled to the base unit of the imaging system and transferred to the toe portion of the imaging system, similar to C-arm 104, base unit 102, and toe portion 157, respectively, described above). The motion/pivoting of the pivot plate 204 induced by the vibrational loads passed into vibration damping assembly 258 are translated into compression and expansion of the damping elements (damping element 306 and springs 602 and 603), as illustrated in FIGS. 3-5, and upon each expansion/contraction of the damping elements a portion of the vibrational energy is absorbed by the components, whereby the amplitude of the vibration decays.

Referring to FIG. 6, an exploded view of the vibration damping assembly 258 is shown. FIG. 6 shows the components of vibration damping assembly 258 vertically displaced relative to each other to more clearly illustrate the components and spatial interrelationships of the components comprising vibration damping assembly 258. FIG. 6 shows openings 604 adapted to receive the respective stops of the vibration damping assembly 258 (e.g., stopper pins 216 and 217). Assembly axes are shown in order to illustrate coupling between various components. For example, wheels 160 are configured to couple to respective openings 214 of the pivot plate 204, spring 602 is configured to seat within opening 305 of biasing member housing 304, spring 603 is configured to seat within opening 307 of biasing member housing 304, damping element 306 is configured to couple in face-sharing contact with upper surface 605 of biasing member housing 304 and the rearward portion 208 of pivot plate 204, and cover plate 301 is configured to couple in face-sharing contact with the forward portion 206 of pivot plate 204. Toe portion 257 is shown with the housing removed for illustrative clarity (e.g., cover 220 shown by FIG. 2 and described above).

To further illustrate the relative positioning of the components of the vibration damping assembly 258, FIG. 7 shows a perspective view of underside 207 of the vibration damping assembly 258 coupled to the toe portion 257, and FIG. 8 shows the underside 207 of the vibration damping assembly 258 with the vibration damping assembly 258 removed from the toe portion 257. FIGS. 7-8 each show the vibration damping assembly 258 in the neutral load condition described above with reference to FIG. 3. As shown by FIG. 8, spring 602 and spring 603 each form an interface between the toe portion 257 and the pivot plate 204, where biasing member housing 304 is adapted to seat within the recess of the toe portion 257, and damping element 306 forms an interface between the pivot plate 204 and the toe portion 257 via the biasing member housing 304. As described above, openings 214 of the pivot plate 204 may be coupled to respective wheels 261 (shown by FIGS. 2-6), such that the pivot plate 204 of vibration damping assembly 258 forms an interface between the damping element 306, toe portion 257, and the ground surface 290 on which the imaging system 200 sits (as shown by FIGS. 2-5).

In this way, the imaging system 200 including the vibration damping assembly 258 may experience reduced amplitude and/or duration of vibrations relative to imaging systems that do not include the vibration damping assembly 258. For example, an imaging system that does not include the vibration damping assembly 258 and instead includes wheels forming an interface directly between a toe portion of the imaging system and a ground surface on which the imaging system sits may be subject to vibrations having a relatively high amplitude and/or relative low vibration decay rate (e.g., a relatively high duration of vibration responsive to a given impulse applied to the imaging system). However, because the imaging system 200 includes the vibration damping assembly 258, vibrations of the imaging system 200 may have reduced amplitude and/or reduced duration for the same given impulse applied to the imaging system 200.

For example, imaging systems that do not include the vibration damping assembly 258 may experience vibrations resulting in a vertical movement (e.g., shifting) of a C-arm of the imaging system by up to 2 millimeters toward and away from the ground surface on which the imaging system sits for a given impulse applied to the imaging system. Further, a duration of the vibrations may be relatively high, such that for imaging purposes the vibrations of the imaging system result in blur of images produced by the imaging system for up to 10 seconds after the given impulse is applied to the imaging system. However, imaging system 200 including the vibration damping assembly 258 may experience vibrations resulting in a vertical movement of the C-arm of the imaging system by a much lower amount, such as 1 millimeter, for the same given impulse. Further, the duration of the vibrations may be relatively low, such that an amplitude of the vibrations is decreased much more quickly. For example, as described above, the imaging system that does not include the vibration damping assembly 258 may vibrate for 10 seconds (or more) after vibration of the imaging system begins (e.g., after the given impulse is applied to the imaging system), whereas vibrations of the imaging system 200 including the vibration damping assembly 258 may cease after a much shorter amount of time (e.g., 4 seconds) after vibration of the imaging system 200 begins. As a result, an imaging quality of the imaging system 200 may be increased, and an imaging time of the imaging system 200 and a likelihood of degradation of components of the imaging system 200 resulting from vibration may be decreased.

A technical effect of positioning a vibration damping assembly as disclosed herein, at an end of an extended toe portion of a cantilevered medical imaging system, is that characteristic vibrations induced by movement of the cantilevered medical imaging components are efficiently transferred into one or more damping elements and converted to heat (increasing a decay rate of the vibration), while reducing the initial amplitude of the vibration by increasing an inertial moment of the medical imaging system.

In one embodiment, a vibration damping assembly for a C-arm imaging system comprises: a pivot element rotatably coupled to a toe portion of the C-arm imaging system and configured to form an interface between the toe portion, a damping element, and a ground surface on which the C-arm imaging system sits. In a first example of the vibration damping assembly, the damping element comprises at least one deformable member engaged with an end of the pivot element. A second example of the vibration damping assembly optionally includes the first example, and further includes wherein the at least one deformable member comprises a spring seated within an opening of a biasing member housing, the spring forming an interface between the toe portion and the pivot element. A third example of the vibration damping assembly optionally includes one or both of the first and second examples, and further includes wherein the at least one deformable member comprises a deformable damping pad forming an interface between the toe portion and the pivot element. A fourth example of the vibration damping assembly optionally includes one or more or each of the first through third examples, and further includes wherein the pivot element includes a pivot pin rotatably coupled to a mounting bracket, the mounting bracket fixedly coupled to the toe portion. A fifth example of the vibration damping assembly optionally includes one or more or each of the first through fourth examples, and further includes wherein the mounting bracket includes a stop configured to limit a rotation of the pivot element in a first direction. A sixth example of the vibration damping assembly optionally includes one or more or each of the first through fifth examples, and further includes wherein the stop is positioned at a first side of the mounting bracket, and the pivot element includes a flange configured to engage with an opposing, second side of the mounting bracket to limit a rotation of the pivot element in an opposing, second direction. A seventh example of the vibration damping assembly optionally includes one or more or each of the first through sixth examples, and further includes a cover plate forming an interface between an end of the pivot element and a cover of the toe portion at a first side of the pivot element, the pivot element rotatably coupled to the toe portion at an opposing, second side.

In one embodiment, a vibration damping assembly for a mobile radiographic imaging system comprises: a first support arm including a first opening and a second support arm including a second opening, with each of the first support arm and second support arm configured to couple to a toe portion of the mobile radiographic imaging system; a pivot plate rotatably coupled to the first support arm and second support arm, the pivot plate including a pivot pin seated within each of the first opening and second opening; and one or more biasing members configured to engage with the pivot plate between an underside of the pivot plate and the toe portion. In a first example of the vibration damping assembly, the one or more biasing members includes a spring and a damping element, with the spring and the damping element coupled to the underside of the pivot plate at a rearward portion of the pivot plate, with an opposing, forward portion of the pivot plate positioned across the pivot pin and configured to couple to one or more wheels of the mobile radiographic imaging system. A second example of the vibration damping assembly optionally includes the first example, and further includes wherein the spring is seated adjacent to the damping element, with the damping element arranged between an upper surface of the biasing member housing and the underside of the pivot plate. A third example of the vibration damping assembly optionally includes one or both of the first and second examples, and further includes a first stop coupled to the first support arm and a second stop coupled to the second support arm, the first stop and second stop configured to limit a rotation of the pivot plate. A fourth example of the vibration damping assembly optionally includes one or more or each of the first through third examples, and further includes a cover plate supported by the pivot plate, the cover plate configured to engage with a cover of the toe portion.

In one embodiment, a medical imaging system comprises: a C-arm including an x-ray source and an x-ray detector; a base unit including a toe portion extending toward the C-arm at a ground surface on which the medical imaging system sits; and a vibration damping assembly configured to damp vibration of the medical imaging system, comprising: a first support arm and a second support arm fixedly coupled to the toe portion; a pivot plate rotatably coupled to the first support arm and second support arm via a pivot pin; a spring arranged between the toe portion and the pivot plate and biasing the pivot plate, the spring housed in a biasing member housing; and a damping element arranged between the biasing member housing and the pivot plate and biasing the pivot plate. In a first example of the medical imaging system, a forward portion of the pivot plate is coupled to one or more wheels supporting a weight of the mobile medical imaging system, and wherein the wheels are affixed to an underside of the forward portion of the pivot plate. A second example of the medical imaging system optionally includes the first example, and further includes wherein the pivot plate includes a first flange and a second flange at a rearward portion opposite to the forward portion, with the first flange configured to engage with the first support arm and the second flange configured to engage with the second support arm to limit a rotation of the pivot plate via the pivot pin. A third example of the medical imaging system optionally includes one or both of the first and second examples, and further includes wherein the biasing member housing is seated within a recess of the toe portion, and the spring engages with the toe portion at the recess. A fourth example of the medical imaging system optionally includes one or more or each of the first through third examples, and further includes wherein in an unloaded condition, the pivot plate is arranged approximately parallel with the first support arm, second support arm, and ground surface. A fifth example of the medical imaging system optionally includes one or more or each of the first through fourth examples, and further includes wherein in a loaded condition, a rotation of the pivot plate via the pivot pin is limited by one or more stops coupled to the support arm. A sixth example of the medical imaging system optionally includes one or more or each of the first through fifth examples, and further includes wherein the loaded condition includes vibrational load applied to the vibration damping assembly through the toe portion.

FIGS. 1-8 show example configurations with relative positioning of the various elements. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example. It will be appreciated that one or more components referred to as being "substantially similar and/or identical" differ from one another according to manufacturing tolerances (e.g., within 1-5% deviation).

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

As used herein, the term "approximately" is construed to mean plus or minus five percent of the range unless otherwise specified.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A vibration damping assembly for a C-arm imaging system, comprising:
a pivot element rotatably coupled to a toe portion of the C-arm imaging system and configured to form an interface between the toe portion, a damping element, and a ground surface on which the C-arm imaging system sits, wherein the pivot element comprises a forward portion coupled to one or more wheels supporting a weight of the C-arm imaging system.

2. The vibration damping assembly of claim 1, wherein the damping element comprises at least one deformable member engaged with an end of the pivot element.

3. The vibration damping assembly of claim 2, wherein the at least one deformable member comprises a spring seated within an opening of a biasing member housing, the spring forming an interface between the toe portion and the pivot element.

4. The vibration damping assembly of claim 2, wherein the at least one deformable member comprises a deformable damping pad forming an interface between the toe portion and the pivot element.

5. The vibration damping assembly of claim 1, wherein the pivot element includes a pivot pin rotatably coupled to a mounting bracket, the mounting bracket fixedly coupled to the toe portion.

6. The vibration damping assembly of claim 5, wherein the mounting bracket includes a stop configured to limit a rotation of the pivot element in a first direction.

7. The vibration damping assembly of claim 6, wherein the stop is positioned at a first side of the mounting bracket, and the pivot element includes a flange configured to engage with an opposing, second side of the mounting bracket to limit a rotation of the pivot element in an opposing, second direction.

8. The vibration damping assembly of claim 1, further comprising a cover plate forming an interface between an end of the pivot element and a cover of the toe portion at a first side of the pivot element, the pivot element rotatably coupled to the toe portion at an opposing, second side.

9. A vibration damping assembly for a mobile radiographic imaging system, comprising:
a first support arm including a first opening and a second support arm including a second opening, with each of the first support arm and second support arm configured to couple to a toe portion of the mobile radiographic imaging system;
a pivot plate rotatably coupled to the first support arm and second support arm, the pivot plate including a pivot pin seated within each of the first opening and second opening; and
one or more biasing members configured to engage with the pivot plate between an underside of the pivot plate and the toe portion.

10. The vibration damping assembly of claim 9, wherein the one or more biasing members includes a spring and a damping element, with the spring and the damping element coupled to the underside of the pivot plate at a rearward portion of the pivot plate, with an opposing, forward portion of the pivot plate positioned across the pivot pin and configured to couple to one or more wheels of the mobile radiographic imaging system.

11. The vibration damping assembly of claim 10, wherein the spring is seated adjacent to the damping element, with the damping element arranged between an upper surface of the biasing member housing and the underside of the pivot plate.

12. The vibration damping assembly of claim 9, further comprising a first stop coupled to the first support arm and a second stop coupled to the second support arm, the first stop and second stop configured to limit a rotation of the pivot plate.

13. The vibration damping assembly of claim 9, further comprising a cover plate supported by the pivot plate, the cover plate configured to engage with a cover of the toe portion.

14. A medical imaging system, comprising:
a C-arm including an x-ray source and an x-ray detector;
a base unit including a toe portion extending toward the C-arm at a ground surface on which the medical imaging system sits; and
a vibration damping assembly configured to damp vibration of the medical imaging system, comprising:
a first support arm and a second support arm fixedly coupled to the toe portion;
a pivot plate rotatably coupled to the first support arm and second support arm via a pivot pin;
a spring arranged between the toe portion and the pivot plate and biasing the pivot plate, the spring housed in a biasing member housing; and
a damping element arranged between the biasing member housing and the pivot plate and biasing the pivot plate.

15. The medical imaging system of claim 14, wherein a forward portion of the pivot plate is coupled to one or more wheels supporting a weight of the mobile medical imaging system, and wherein the wheels are affixed to an underside of the forward portion of the pivot plate.

16. The medical imaging system of claim 15, wherein the pivot plate includes a first flange and a second flange at a rearward portion opposite to the forward portion, with the first flange configured to engage with the first support arm and the second flange configured to engage with the second support arm to limit a rotation of the pivot plate via the pivot pin.

17. The medical imaging system of claim 14, wherein the biasing member housing is seated within a recess of the toe portion, and the spring engages with the toe portion at the recess.

18. The medical imaging system of claim 14, wherein in an unloaded condition, the pivot plate is arranged approximately parallel with the first support arm, second support arm, and ground surface.

19. The medical imaging system of claim 14, wherein in a loaded condition, a rotation of the pivot plate via the pivot pin is limited by one or more stops coupled to the support arm.

20. The medical imaging system of claim 19, wherein the loaded condition includes vibrational load applied to the vibration damping assembly through the toe portion.

* * * * *